United States Patent
Moran, Jr.

(10) Patent No.: US 10,018,645 B2
(45) Date of Patent: Jul. 10, 2018

(54) IMMUNODIAGNOSTIC TEST ELEMENT HAVING WEAKENED FOIL LAYER

(71) Applicant: Ortho-Clinical Diagnostics, Inc., Rochester, NY (US)

(72) Inventor: Donald J. Moran, Jr., Rochester, NY (US)

(73) Assignee: ORTHO-CLINICAL DIAGNOSTICS, INC., Raritan, NJ (US)

( * ) Notice: Subject to any disclaimer, the term of this patent is extended or adjusted under 35 U.S.C. 154(b) by 0 days.

(21) Appl. No.: 15/420,559

(22) Filed: Jan. 31, 2017

(65) Prior Publication Data

US 2017/0138977 A1    May 18, 2017

Related U.S. Application Data

(62) Division of application No. 12/054,790, filed on Mar. 25, 2008, now Pat. No. 9,562,921.

(51) Int. Cl.
*B01L 3/00* (2006.01)
*G01N 35/00* (2006.01)
(Continued)

(52) U.S. Cl.
CPC ........ *G01N 35/1079* (2013.01); *B01L 3/5021* (2013.01); *B01L 3/5025* (2013.01);
(Continued)

(58) Field of Classification Search
CPC ......... B01L 2200/026; B01L 2300/044; B01L 2400/0409; B01L 2400/0683;
(Continued)

(56) References Cited

U.S. PATENT DOCUMENTS

| 4,195,731 A | 4/1980 | Cavazza | 206/222 |
| 4,386,925 A | 6/1983 | Focke | 493/338 |

(Continued)

FOREIGN PATENT DOCUMENTS

| DE | 3921592 | 1/1991 |
| DE | 4329931 A1 | 3/1995 |

(Continued)

OTHER PUBLICATIONS

Indian Examination Report for IN 3916/KOLNP/2010; dated Aug. 28, 2017; 5 pages.

(Continued)

*Primary Examiner* — Jennifer Wecker
(74) *Attorney, Agent, or Firm* — K&L Gates LLP; Louis C. Cullman; Joseph Arand (57) ABSTRACT

An immunodiagnostic test element includes a support member, at least one test column containing a test material, and a wrap, such as an adhesively-attached foil wrap, covering the top of the at least one test element. The wrap includes a weakened portion directly above each test column, in which each weakened portion is formed by pre-stressing the portion, but not to the point of puncturing the wrap to enable the wrap to be punctured by a fluid aspirating/dispensing element, such as a metering tip, permitting access to the contents of the test column.

13 Claims, 6 Drawing Sheets

(51) Int. Cl.
*G01N 35/10* (2006.01)
*B01J 19/00* (2006.01)

(52) U.S. Cl.
CPC ... *B01L 2200/026* (2013.01); *B01L 2300/044* (2013.01); *B01L 2400/0409* (2013.01); *B01L 2400/0683* (2013.01); *Y10T 436/11* (2015.01)

(58) Field of Classification Search
CPC . B01L 3/5021; B01L 3/5025; G01N 35/1079; Y10T 436/11
See application file for complete search history.

(56) References Cited

U.S. PATENT DOCUMENTS

| | | | |
|---|---|---|---|
| 4,519,513 A | 5/1985 | Weiler et al. | 215/48 |
| 4,905,886 A | 3/1990 | Kennedy et al. | |
| 5,188,628 A | 2/1993 | Rani et al. | 604/405 |
| 5,330,899 A | 7/1994 | DeVaughn | |
| 5,512,432 A | 4/1996 | LaPierre et al. | |
| 5,578,269 A * | 11/1996 | Yaremko | G01N 35/025 210/361 |
| 5,589,063 A | 12/1996 | Sanford et al. | |
| 5,780,248 A | 7/1998 | Milchanoski et al. | |
| 5,911,000 A | 6/1999 | Shen | |
| 6,030,582 A | 2/2000 | Levy | |
| 6,033,913 A | 3/2000 | Morozov et al. | |
| 6,274,087 B1 | 8/2001 | Preston et al. | |
| 6,627,156 B1 | 9/2003 | Goodale et al. | |
| 6,881,579 B2 | 4/2005 | Hilson et al. | |
| 7,100,460 B2 | 9/2006 | Özbal | |
| 7,164,107 B2 | 1/2007 | Bedingham et al. | |
| 7,854,896 B2 | 12/2010 | Tyndorf et al. | |
| 2005/0079320 A1 | 4/2005 | Birk | |
| 2005/0136207 A1 | 6/2005 | Moosheimer et al. | |
| 2005/0244972 A1 | 11/2005 | Hilson et al. | |
| 2006/0032746 A1 | 2/2006 | Knott et al. | |
| 2006/0118434 A1* | 6/2006 | Leiner | B65D 81/3266 206/219 |
| 2007/0034592 A1 | 2/2007 | Pavlovic et al. | |
| 2007/0036684 A1 | 2/2007 | Burkhardt et al. | |
| 2009/0191641 A1* | 7/2009 | Chiapperi | B01L 3/5025 436/69 |

FOREIGN PATENT DOCUMENTS

| | | |
|---|---|---|
| EP | 0 527 562 A2 | 2/1993 |
| EP | 0 527 562 A3 | 2/1993 |
| EP | 895088 A2 | 2/1999 |
| EP | 1 894 653 A1 | 3/2008 |
| JP | 08-192489 | 7/1996 |
| JP | 3050685 | 5/1998 |
| JP | 2003-522318 | 7/2003 |
| JP | 2003-267407 A | 9/2003 |
| JP | 2005-514287 | 5/2005 |
| WO | WO 91/02976 | 3/1991 |
| WO | WO 99/45360 | 9/1999 |
| WO | WO 03/059777 A1 | 7/2003 |
| WO | WO 2004101153 A1 | 11/2004 |
| WO | WO 2006/094388 A1 | 9/2006 |
| WO | WO 2007/130846 A2 | 11/2007 |
| WO | WO 2007/130846 A3 | 11/2007 |

OTHER PUBLICATIONS

Japanese Office Action for JP 2013-167391; dated Nov. 24, 2015; 3 pages.
Japanese Office Action for JP 2013-167391: dated Aug. 5, 2014, 4 pages.
Japanese Office Action for JP Application No. 2011-501898: dated Jan. 15, 2013, 3 pages.
International Search Report and Written Opinion for International PCT Patent Application No. PCT/US2009/037051; dated Jun. 18, 2009; 10 Pages.
Japanese Utility Model Registration 3050685, 2003, pp. 1-8, translation.
PCT Application Japanese Translation Publication 2003-522318, 2003, pp. 1-17, translation.
Merchant et al, "Bendability of Thin Copper Foil", IPC Printed Circuits EXPO, Long Beach, CA, Apr. 1998, pp. 1-9; http://www.gould.com/e4/e139/e197/tpyear198/tpdownload251/BEND_eng.PDF.

* cited by examiner

IMMUNODIAGNOSTIC TEST ELEMENT HAVING WEAKENED FOIL LAYER

CROSS REFERENCE TO RELATED APPLICATION

This application is a divisional application of U.S. Ser. No. 12/054,790, filed on Mar. 25, 2008, the entire contents of which is incorporated by reference.

FIELD OF THE INVENTION

The application relates to the field of immunodiagnostic testing and in particular to an immunological test element having at least one test chamber and covered by a pierceable foil layer. The foil layer is defined by at least one weakened portion that permits puncture, such as by a fluid dispensing and aspirating element, in order to facilitate access to the contents of the test chamber.

BACKGROUND OF THE INVENTION

Immunological agglutination reactions are presently used for identifying various kinds of blood types as well as for detecting various kinds of antibodies and antigens in blood samples and other aqueous solutions. In such procedures, a sample of red blood cells is mixed with serum or plasma in either test tubes or microplates, wherein the mixture is incubated and then centrifuged. Various reactions then occur or do not occur depending on, for example, the blood types of the red blood cells or whether certain antibodies are present within the blood sample. These reactions manifest themselves as clumps of cells or as particles with antigens or antibodies on their surfaces, referred to as agglutinates. The failure of any agglutinates to appear indicates no reaction has occurred, while the presence of agglutinates, depending on the size and amount of the clumps formed, indicates the presence of a reaction and the level of concentration of cells and antibodies in the sample and reaction strength.

As described, for example, in U.S. Pat. No. 5,512,432 to LaPierre et al., and rather than using microplates or test tubes, another form of agglutination test method has been developed and successfully commercialized. According to this method, gel or glass bead microparticles are contained within a small column, referred to as a microcolumn or a microtube. A reagent, such as anti-A, is dispensed in a diluent in the microcolumn and test red blood cells are placed in the reaction chamber above the column. The column, which is typically one of a plurality of columns formed in a transparent card or cassette, is then centrifuged. The centrifugation accelerates the reaction, if any, between the red blood cells and the reagent, and also urges any cells toward the bottom of the column. In the meantime, the glass beads or the gel material acts as a filter, and resists or impedes downward movement of the particles in the column. As a result, the nature and distribution of the particles in the microcolumn provides a visual indication of whether any agglutination reaction has occurred, and if such a reaction has occurred, the strength of the reaction based on the relative position of the agglutinates in the column. If no agglutination reaction has occurred, then all or virtually all of the red blood cells in the microtube will pass downward during the centrifugation procedure, to the bottom of the column in the form of a pellet. Conversely and if there is a strong reaction between the reagent and the red blood cells, then virtually all of the red blood cells will agglutinate, and large groupings will form at the top of the microtube above the gel or bead matrix in that the matrix is sized not to let these clumps pass through. Reactions falling between these latter two extremes are possible in which some but not all of the red blood cells will have agglutinated. The percentage of red blood cells that agglutinate and the size of the agglutinated particles each have a relationship with the strength of the reaction. Following the centrifugation process and after all processing steps have been completed, the microtube is visually examined by either a human operator or by machine vision and the reaction between the red blood cells and the reagent is then classified. The reaction is classified as being either positive or negative, and if positive, the reaction is further classified into one of four classes depending on the strength of the reaction.

Currently, so-called gel cards and/or bead cassettes are known test elements that employ a plurality of microtubes for purposes of creating agglutination reactions as described above for purposes of blood grouping, blood typing, antigen or antibody detection and other related applications and uses. These test elements commonly include a planar substrate that supports a plurality of transparent columns or microtubes, each of the columns containing a quantity of an inert material, such as a gel material or a plurality of glass beads, respectively, that is disposed in an aqueous slurry that includes an antibody or antigen or is provided with a carrier-bound antibody or antigen, each of the foregoing being provided by the manufacturer. A pierceable wrap completes the assembly of the test element, the wrap, which may be, for example, in the form of an adhesively or otherwise-attached foil wrap, covering the top side of the test element, in order to cover the contents of each column. Once pierced, aliquots of patient sample and possibly reagents (e.g., if reagents are not first added by the manufacturer or additional reagents, depending on the test) can be added to the columns, either manually or using automated apparatus. The test element thus containing patient sample (e.g., red blood cells and sera) is then incubated and following incubation, the test element is spun down by centrifugation, as noted above, in order to accelerate an agglutination reaction that can be graded either based on the position of agglutinates within each transparent column of the test element or cassette or due to a lack of agglutination based on the cells settling at the bottom of the test column.

As noted, each of these test elements include a foil wrap disposed at the top of the card or cassette covering the columns wherein the wrap can be pierced prior to the dispense of the patient sample, reagents, or other material into at least one microtube of the test element. The foil wrap forms a seal relative to the contents of the columns to prevent contamination and also prevents the contents of the columns from drying out or degrading.

A number of automated or semi-automated apparatus, such as those manufactured by Ortho-Clinical Diagnostics, Inc., DiaMed A.G., and Grifols, are known that utilize plurality of gel cards or bead cassettes, such as those manufactured and sold by Micro-Typing Systems, Inc., DiaMed A.G., and BioRad, among others. Typically, these apparatus employ separate assemblies to accomplish the piercing function. In one known version, a pipette assembly probe is used to directly puncture the foil wrap. Using the metering probe for puncture wherein contact is made with the contents of the test columns means that this probe must undergo a separate washing operation following the piercing step before use thereof can be resumed to avoid contamination. In addition to potential contamination issues, there are also related issues dealing with spillage as well as fluidic carryover. In addition, washing operations add levels of complexity to the size and manufacture of the apparatus as well as hinder potential throughput time. In another known apparatus, a piercing assembly is provided having a plurality of dedicated puncture elements used to puncture the seals for each of the test chambers of a test element. This dedicated apparatus also adds a level of complexity, including an increase to the size of the overall footprint of the apparatus. The latter assembly also requires washing operations of the puncture elements themselves prior to any re-use thereof. Furthermore, the latter puncture assembly operates with only a fixed number of configurations wherein typically all of the test columns of the test card are punctured, even for tests in which certain columns are not necessarily required. Still other test elements are accessed by removal of the entire foil strip prior to processing.

SUMMARY OF THE INVENTION

According to one aspect, there is provided an immunodiagnostic test element comprising a substrate, at least one test column supported by said substrate, each said test column containing a test material, and a wrap adhesively or otherwise-attached wrap covering the top of said at least one test element, such as, for example, an adhesively-attached foil wrap wherein said foil wrap includes a weakened portion directly above each said at least one test column, each said weakened portion being formed by pre-stressing said portion, but not to the point of puncturing the foil wrap.

By providing at least one pre-stressed portion, the foil wrap is drastically weakened locally, thereby enabling each pre-stressed portion to be easily punctured, for example, using a disposable fluid aspirating dispensing member, such as a metering tip. Moreover, the pre-stressed portions are also locally deformed and assume a bowl-like concave shape. Alternatively, the pre-stressing can be performed on the wrap prior to covering of the test element with the wrap.

According to another aspect, there is provided a method for using a test element to enable the test element to be used in conjunction with a disposable metering element, said method comprising the steps of: providing a test card, said test card including a support member, at least one test column attached to or integral to said support member and a wrap, such as, for example, a foil wrap, covering the top side of said at least one test card; and prestressing at least one portion of the foil wrap directly above the contents of said at least one test column, but without puncturing the foil wrap, wherein said pre-stressing step creates a weakened portion. Alternatively, the pre-stressing step can be performed on the wrap prior to the covering of the test element with the wrap.

The above method additionally includes the step of performing the pre-stressing step prior to testing said test element, said prestressing step being performed within an immunodiagnostic testing apparatus by means of at least one of a metering probe and a dedicated mechanism.

The pre-stressed portion causes local deformation of the foil wrap, creating an indentation that is inwardly curved, forming a substantially bowl-like appearance. This portion can then be easily punctured by a separate element. According to one version, a disposable fluid aspirating/dispensing element can be used in lieu of a metering probe to puncture the weakened foil wrap. This disposable element can be used in order to puncture the foil seal and dispense patient sample in a single operation.

One advantage that is realized by the present invention is that contamination within an automated immunodiagnostic testing apparatus is markedly reduced. In addition, the mechanism that creates the weakened pre-stressed portion of the foil wrap does not require a separate washing operation in that this mechanism does not contact any of the contents of the test element.

Moreover, the geometry of the weakened foil wrap portion provides a bowl-like feature that reduces the incidence of splashing or drainage of sample or reagent into adjacent wells or columns.

The herein described apparatus and method provides considerable cost savings as well as considerable improvements in throughput when used in conjunction with an automated apparatus.

In addition, the number of punctures made to any given test element can easily be varied wherein all or only some of the test columns can be accessed. Therefore, the system is not limited to a fixed number of configurations, thereby providing increased versatility over prior systems.

Use of a metering tip for purposes of puncturing the pre-stressed test element reduces the overall complexity of an automated apparatus in that washing modules or supplies are no longer required. In addition, risk of contamination or fluidic carryover is significantly reduced.

These and other features and advantages will become readily apparent from the following Detailed Description, which should be read in conjunction with the accompanying drawings.

DETAILED DESCRIPTION

The following discussion relates to certain exemplary embodiments of an immunodiagnostic test element, in this case a gel card or bead cassette. It will be readily apparent to those of skill in the field that the inventive concepts described herein also relate to literally any other form of immunodiagnostic test element that includes at least one test chamber and a wrap, such as, for example, a foil wrap, which covers the at least one test chamber. In addition, certain terms are used throughout this discussion in an effort to provide a frame of reference with regard to the accompanying drawings. These terms should not be regarded as limiting, except where so specifically indicated.

Figure 1:
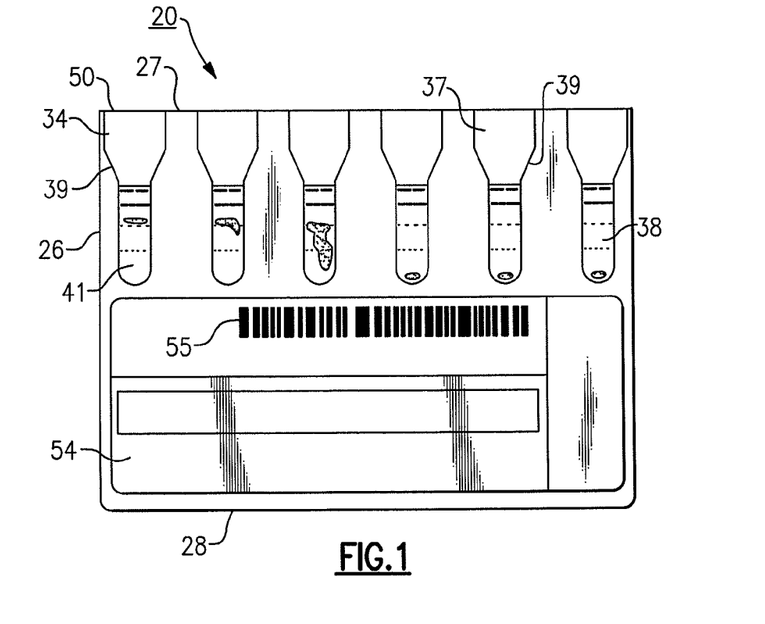
FIGS. 1 and 2 are front views of a pair of prior art immunodiagnostic test elements.
Figure 2:
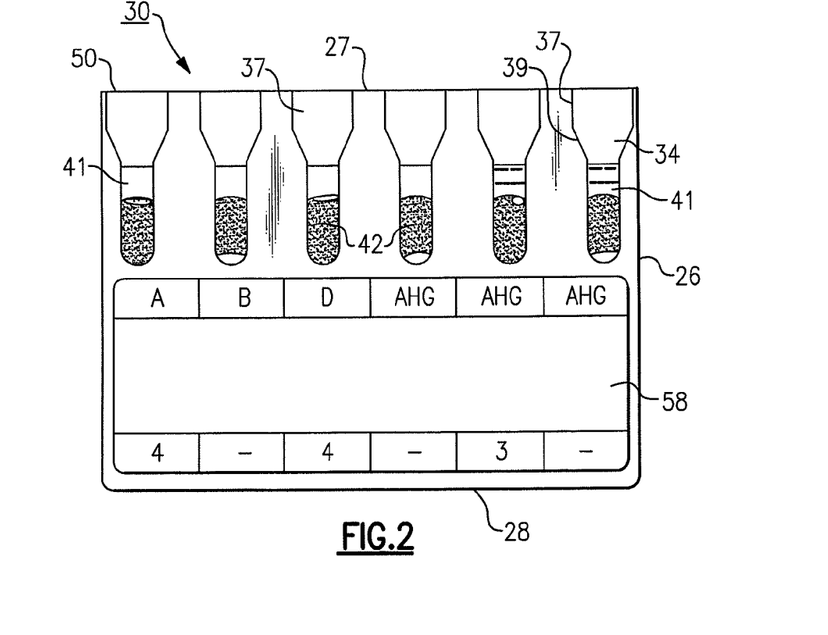

For purposes of background, FIGS. 1 and 2 illustrate a pair of prior art immunodiagnostic test elements. More specifically, FIG. 1 depicts a gel card 20 while FIG. 2 depicts a bead cassette 30. Each of the test elements 20, 30 include a number of common structural features. That is, each test element 20, 30 commonly includes a support member 26 in the form of a planar substrate having a top side 27 and a bottom side 28, wherein the substrate supports a plurality of microtubes or test columns 34. The microtubes 34 are made from a transparent material and are further defined by an upper portion 37 having an open top opening, an inwardly tapering transitional portion 39 and a lower portion 41. A predetermined quantity of an inert material 38, 42, is contained within the lower portion 41 of each test column 34, as typically provided by a manufacturer. In the instance of the gel card 20, the inert material 38 is a gel material, such as Sephacryl or other suitable material, while in the instance of the bead cassette 30, the inert material 42 is defined by a matrix of glass or other beads. Each of the inert material 38, 42 is typically defined by a plurality of particles having a diameter of between about 10 and 100 microns. Typically, an antibody or an antigen or carrier bound antigen or antibody is provided to the inert material 38, 42 contained in each microtube 34 in an aqueous slurry or suspension, also typically provided by the manufacturer. A pierceable foil wrap 50 provided at the top side 27 of each test element 20, 30 covers that seals the microtubes 34 in order to protect the contents and also to prevent dehydration or degrading thereof.

Figure 3:
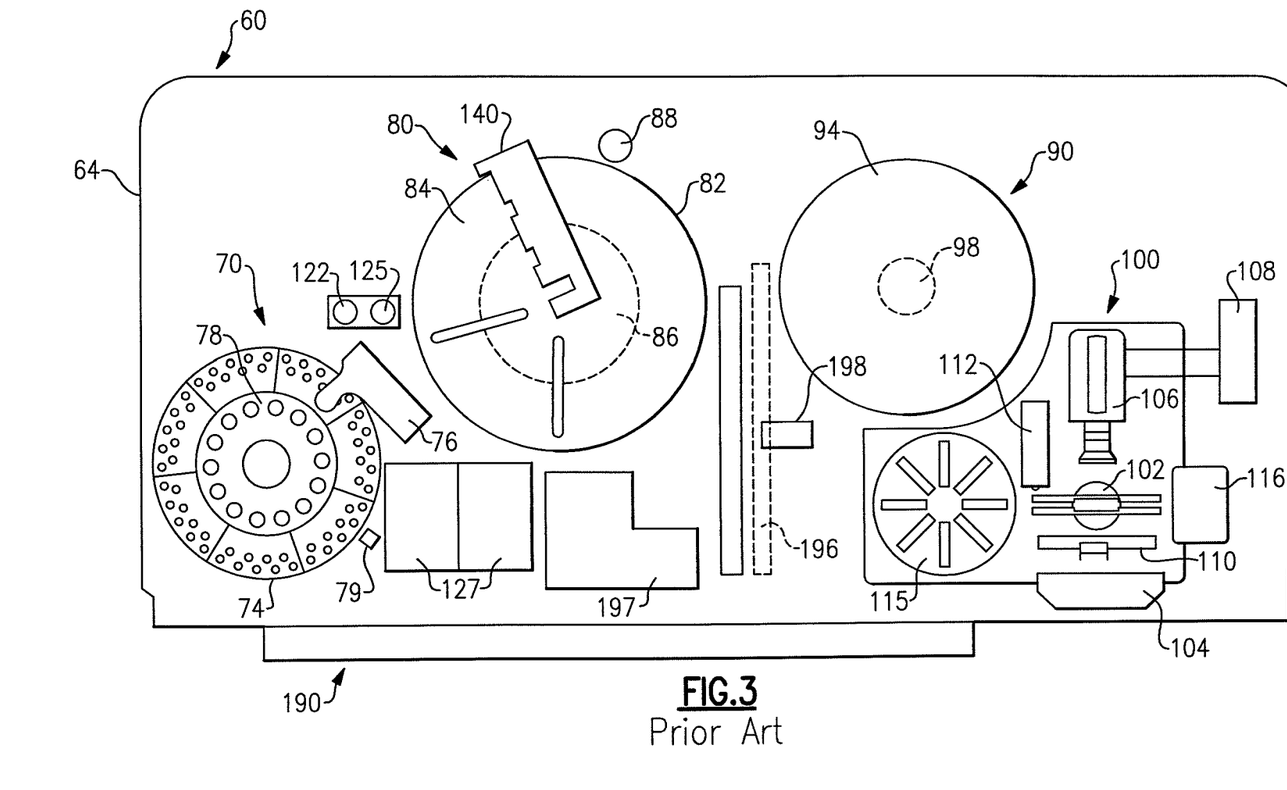
FIG. 3 is a partial top perspective view of a prior art immunodiagnostic testing apparatus.
Figure 4:
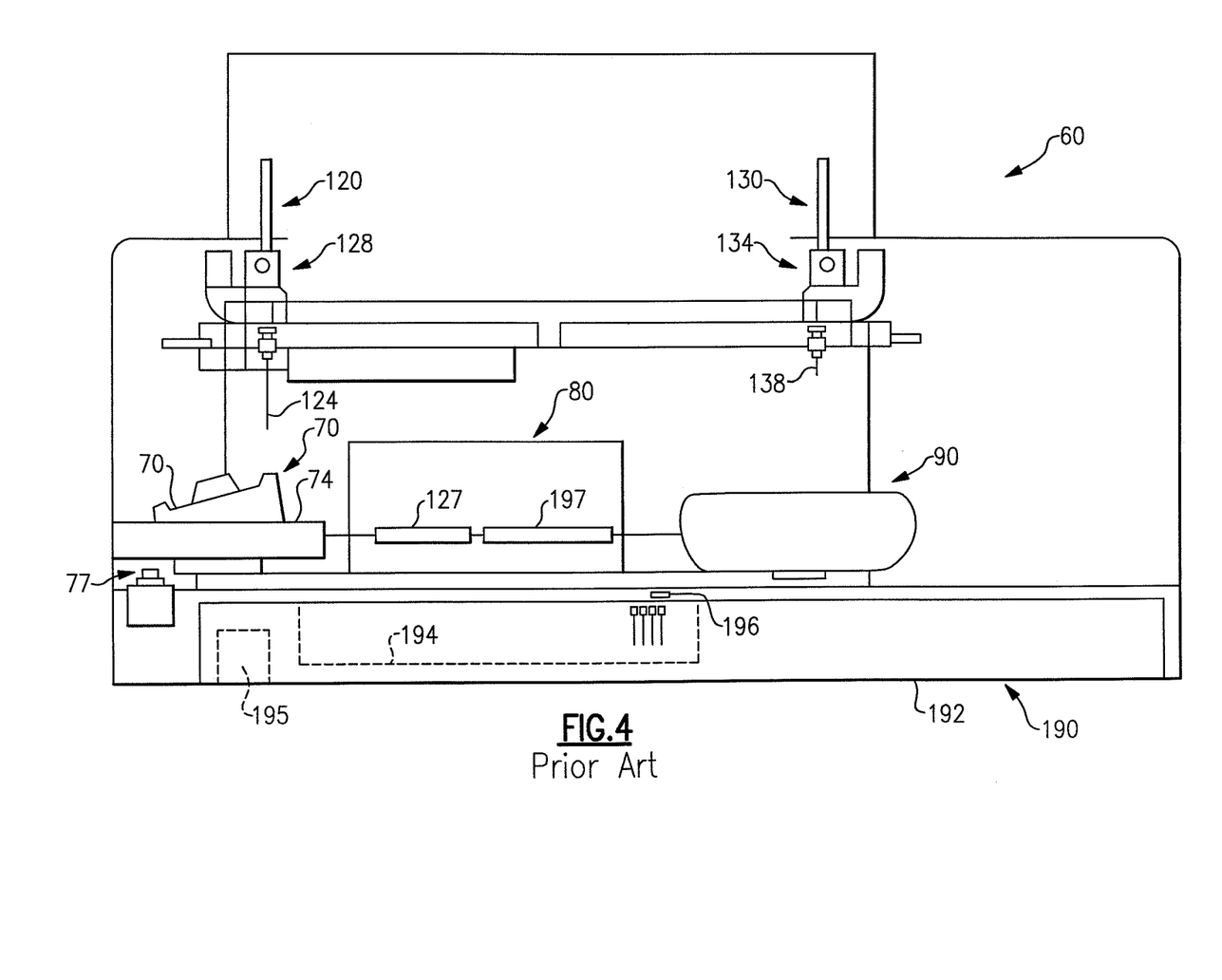
FIG. 4 is a simplified front view of the testing apparatus of FIG. 3.
Figure 5:
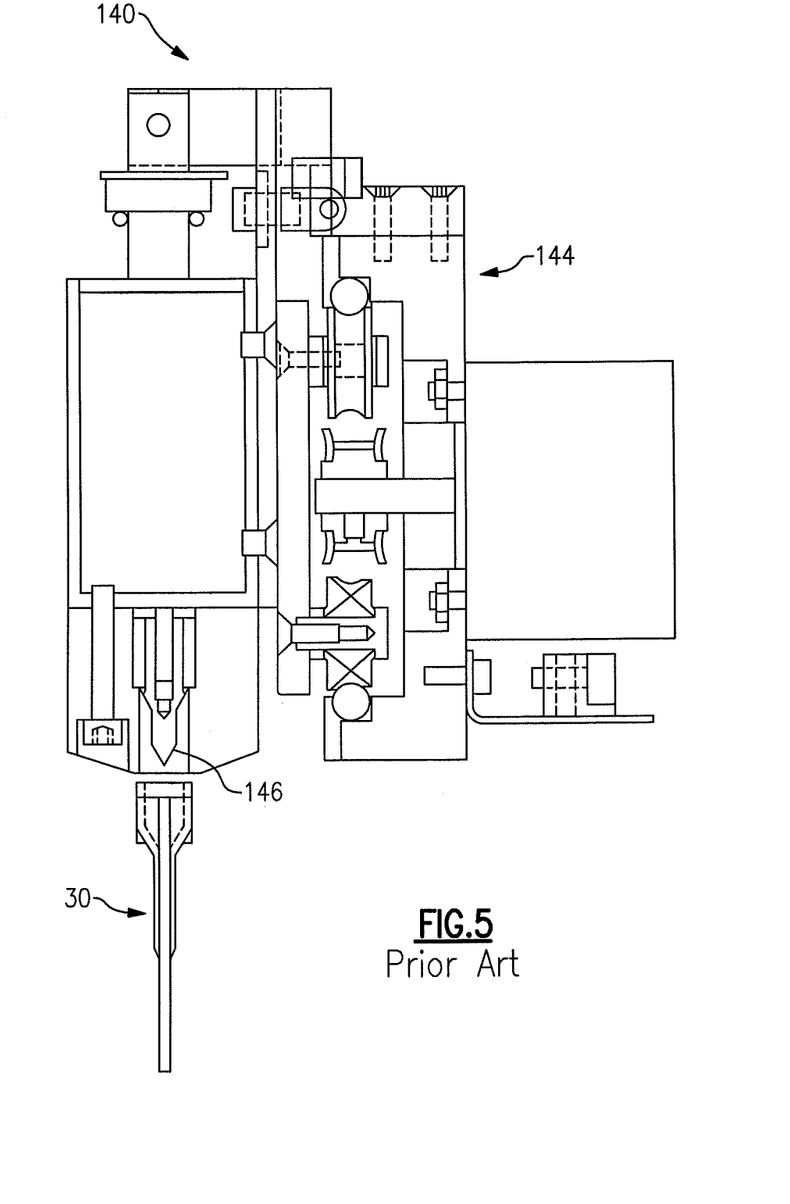
FIG. 5 is a partial side elevational view of the piercing assembly of the prior art immunodiagnostic testing apparatus of FIG. 3.

The foregoing immunodiagnostic test elements 20, 30 can be used in an automated testing apparatus 60, such as that shown in FIGS. 3-5. In brief, the testing apparatus 60 is defined by a frame 64 that retains a number of components including a reagent and sample supply 70, an incubator station 80, a centrifuge 90, an analysis station 100, and a drawer assembly 190, each shown in FIG. 3. More particularly, the sample and reagent supply 70 of this apparatus 60 includes a sample rack 74 as well as a reagent rack 78, each of which contain bottles or vials of patient sample and reagent, respectively. The supply is constructed as a rotor that is rotatable about a center axis by means of a drive mechanism that includes a motor 77, FIG. 4, wherein a bar code reader 79 is further provided in relation to the supply 70 as well as a tube hold-down assembly 76 disposed over a portion thereof. The incubator station 80 includes a cassette rack 82 that further includes respective first and second sections 84, 86, as well as a drive mechanism that includes a motor 88. The centrifuge 90 includes a rotor 94 and a motor 98. The analysis station 100 includes holding means 102, illumination means 104, an imaging subsystem 106, a processing subsystem 108, a transport subsystem 110, a storage rack 115, a bar code reader 112, and a waste receptacle 116. The drawer assembly 190 includes a drawer 192, FIG. 4, a slide tray 194, FIG. 4, a motor 195, a sensor bar 196, a bar code reader 198 and a holding area 197. A transport assembly 130, FIG. 4, of the testing apparatus 60 includes a robot arm 134, FIG. 4, and a gripper 138, FIG. 4. Finally, a pipette assembly 120, FIG. 4, includes a pipette 124, FIG. 4, attached to a robot arm 128, FIG. 4, this assembly further including shallow and deep wash areas 122, 125, as well as cell dilution packs 127.

In the testing apparatus 60 shown, for example, a plurality of test elements 30, such as those previously described according to either FIG. 1 or 2, are initially supported within the drawer 192 and are read by the bar code reader 198. Assuming the read is successful, the test elements 30 are loaded by means of the transport assembly 130 and the gripper 138 into the cassette rack 82 of the incubator 80. A piercing assembly 140, FIG. 5, is disposed above the first and second sections 84, 86 of the cassette rack 82 of the incubator 80 and includes a support subassembly 144 that includes a slide support 145, FIG. 5, having a plurality of puncture needles 146, FIG. 6, that are reciprocably movable, such as by means of solenoids (not shown). The incubator 80, as driven by the motor 88, is used to incubate patient sample added to each of the test columns from one of the vials of the sample rack 65, the incubator further including an assembly 76 that holds down the sample and reagent vials. The pipette 124 of the pipette assembly 120 is used to aspirate sample from the sample rack 65, while the piercing assembly 140, FIG. 5, is used to puncture each of the microtubes of the then-incubated test elements 30. Once the puncturing step has been completed as shown by the test elements shown in FIGS. 6 and 7, the pipette 124 can then be used to dispense a predetermined quantity of patient sample (and possibly additional reagents) from the sample and reagent supply 70 into each of the test columns 34, FIG. 2, wherein the mixture can be suitably incubated.

Following incubation and in the described testing apparatus 60, the test elements 30 are removed from the incubator 80 by means of the transport assembly 130 to the centrifuge 90 wherein the test elements 30 are then spun down, thereby accelerating an agglutination reaction as red blood cells are clumped together in the presence of coated reagents. The plurality of beads disposed in each column of the test element 30 includes particles having diameters ranging between about 10 and 100 microns, providing a matrix for the red blood cells, but not the heavier formed agglutinates to pass through by filtering. The resulting reaction can be imaged within the analysis station 100 of the apparatus 60 by means of the illumination assembly 104 and imaging subsystem 106, the latter being connected to the processing subsystem 108 having machine vision for grading of the reaction. Additional details concerning the foregoing testing apparatus 60 are provided in commonly-assigned U.S. Pat. No. 5,578,269 to Yaremko et al., the entire contents of which are herein incorporated by reference.

Figure 6:
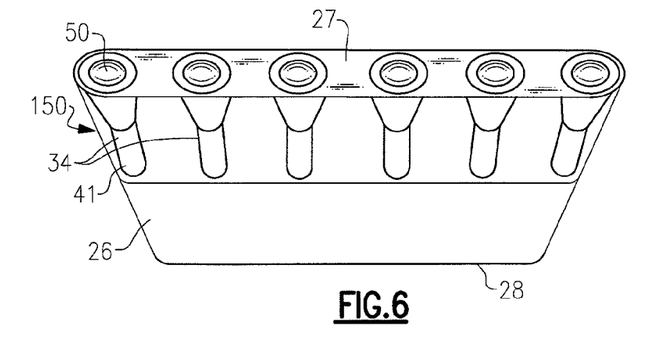
FIGS. 6 and 7 depict top perspective and top plan views of a test element made in accordance with one embodiment prior to piercing of the pre-weakened portions of the foil wrap.
Figure 7:
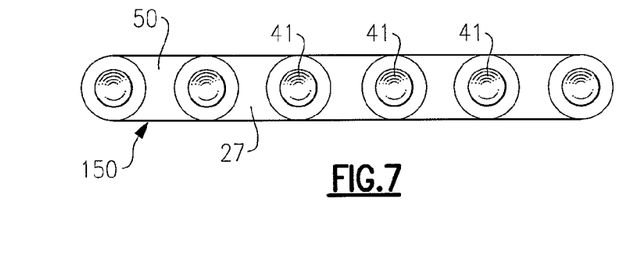

With the preceding being provided as background a test element 150 is shown in FIGS. 6 and 7, in accordance with one embodiment. For the sake of clarity, features that are similar to those previously described with regard to FIGS. 1 and 2 are labeled with the same reference numerals for the sake of clarity. Test element 150 includes a planar substrate 26 having a top side 27 and an opposing bottom side 28 wherein the substrate supports a plurality of transparent microtubes 34. The substrate 26 and microtubes 34 are preferably each made from a lightweight durable plastic material, such as polystyrene, polyamide, acrylic or other suitable material. Each of the microtubes 34 is defined by an open top opening formed in an upper portion having a diameter that is substantially larger than that of a lower portion 41, the upper and lower portions being linked by an inwardly transitioning transitional portion 39 to form a test chamber that contains a quantity of an inert material, in this instance, a matrix of glass beads having a diameter between about 10 and 100 microns. A foil wrap 50 is adhesively or otherwise attached to the top side 27 of the test element 110.

Unlike the previously known test element 30, however, the test element 150 and specifically the foil wrap 50 is further defined by a plurality of weakened portions 154 formed therein. Each of the weakened portions 154 are formed in a section that is disposed directly above the upper portion of each transparent microtube 34.

Referring to FIGS. 10-13, a test element 150 is shown, depicting sequentially one technique for forming the above-noted weakened or pre-stressed portions 154. As noted previously, the test element 150 has at least one microtube 34 supported by the planar substrate 26 that contains a predetermined quantity of an inert test material such as gel material or glass beads (not shown in these views). A foil seal 50 is secured onto the top side of the test element 150, preferably by adhesive or other bonding means.

Still referring to FIGS. 10-13, the following example can be performed within an automated testing apparatus such as the apparatus previously discussed with regard to FIGS. 3-5 or can be performed manually. In each of these views beginning with FIG. 10, the test element 110 is not shown as supported, but would be supported, for example, within an incubator 68, FIG. 3, as described in previously cross-referenced and commonly-assigned U.S. Pat. No. 5,578,269 to Yaremko et al., in a known manner.

Figure 11:
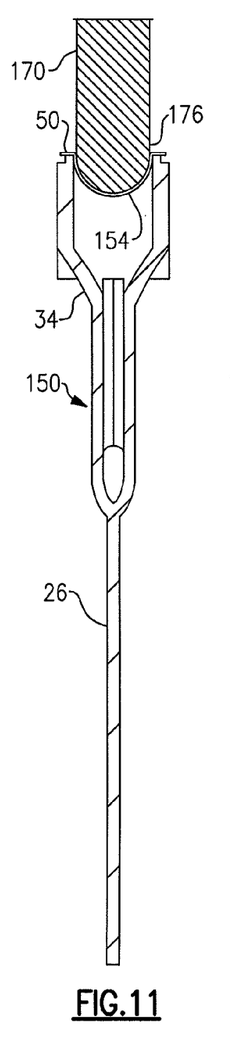

Referring to FIG. 11, a punch 170 or other element is used to locally prestress the foil layer 50 immediately above each microtube 34 of the test element 150. In this manner, the punch 170 does not puncture the layer 50, but rather merely locally deforms a portion 154 of the foil layer 50 inwardly towards the interior of the column given that there is no resisting surface acting against the force of the punch. As a result, the weakened portion 154 assumes a inwardly-curved bowl-like shape. In this example, a shaped punch head 176 having a concave configuration is used to perform this operation. Alternatively, other apparatus could be used for purposes of creating each pre-weakened portion 154. For example, the metering probe of the automated apparatus could alternatively be used in terms of this operation. The punch 170 is then raised and moved out of position, leaving the test element 150 as shown in FIG. 12.

Figures 12, 13:
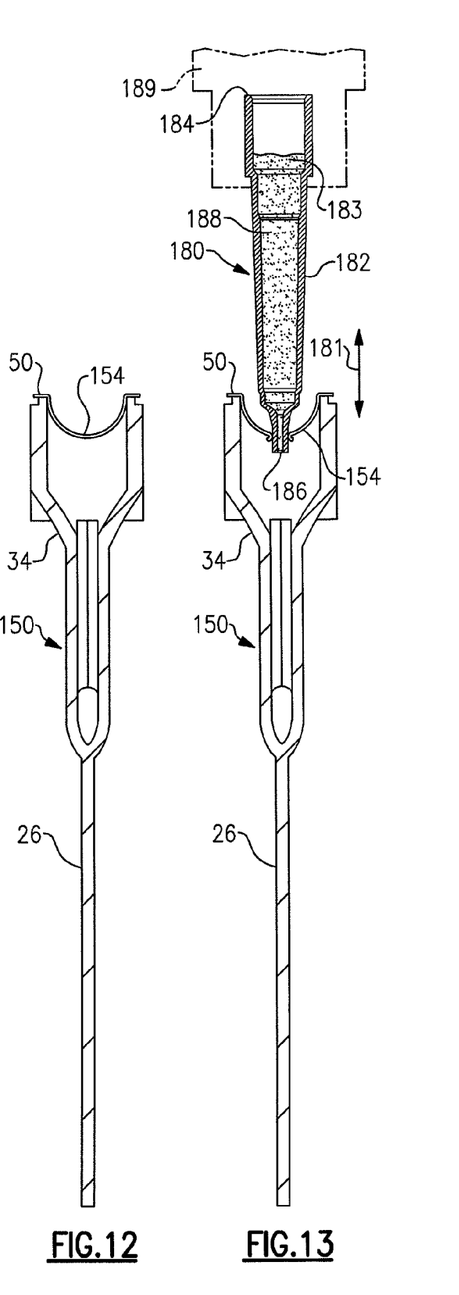

Following this step and referring to FIG. 13, the weakened portion 154 of the foil layer 50 can actually be punctured to permit access to the contents of the test chamber(s). According to this specific embodiment, puncture can be done using a metering tip member, such as a Vitros™ metering element manufactured by Ortho-Clinical Diagnostics, Inc. The metering tip member 180 is disposable, being made from a plastic material and defined by a tapering cylindrical body 182. The tip member 180 is further defined by an upper tip opening 184, a lower tip opening 186 and an interior 188. In this example, the metering tip member 180 is shown as attached to a metering mechanism 189 (shown diagrammatically in FIG. 13) that includes a proboscis that is attached to the upper tip opening 184 of the tip member. The tip member 180 retains a quantity of patient sample 183 or other fluid within its interior 188 that is aspirated from a supply such as the sample and reagent supply 70, FIG. 3, within the testing apparatus 60, FIG. 3. The metering mechanism 189 includes a stepper motor that enables the proboscis and attached tip member 180 to also be moved vertically in the direction of arrow 181, enabling the tip member to be moved into a position to permit the tip member to be lowered in order to puncture the weakened portion 154 of the foil layer 50 and access the interior of each microtube 34 of the test element 150 as shown in FIG. 13. In addition, the metering tip member 180, by already containing a quantity of patient sample 183 from the patient sample supply 70, FIG. 3, of the apparatus 60, FIG. 3, can actually perform both the puncturing and dispensing steps in a continuous operation, thereby significantly improving throughput in a suitably equipped apparatus. In addition, the inwardly curved shape of each weakened portion 154 provides another advantage by reducing the incidence of splashing or cross-contamination between adjacent column.

Figure 8:
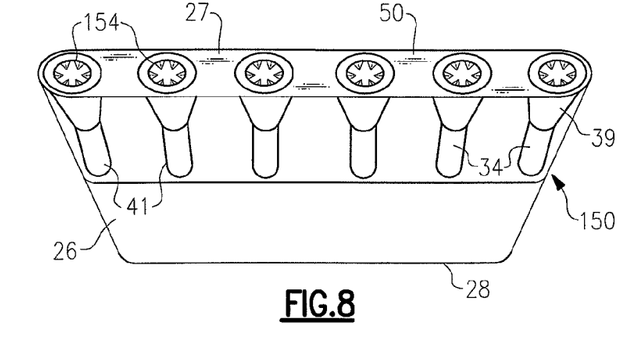
FIGS. 8 and 9 depict top perspective and top plan views of the test element of FIGS. 6 and 7 following piercing of the pre-weakened portions.
Figure 9:
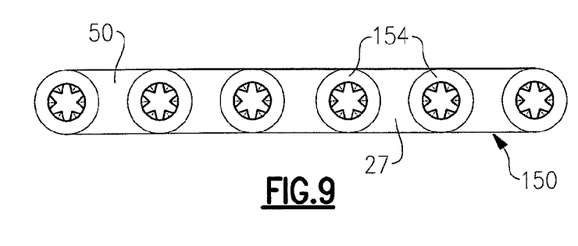
Figure 10:
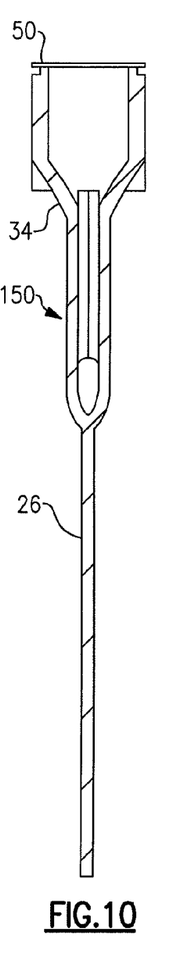
FIGS. 10-13 depict side views of a test column of the immunodiagnostic test element of FIGS. 8 and 9, sequentially illustrating a process of adding a weakened feature to the foil wrap, as well as a subsequent punching step in accordance with an embodiment to permit access to the contents of the test column by means of a metering tip member.

Referring to FIGS. 8 and 9, the test element 150 is shown following puncture of the pre-weakened portions 154 by means of the metering tip member 180, FIG. 13, wherein each of the multiple punctures as shown are highly repeatable in terms of their geometry and size. This repeatability reduces the chance of spillage or cross-contamination between adjacent columns of the test element 150.

Once the metering tip member 180 has dispensed a quantity of patient sample, the tip member can be withdrawn from the test element 150 and discarded, such as through a drop chute (not shown) or other disposal means. Similar operations can be performed for each of the remaining microtubes 34 of the test element 150 prior to test wherein each of the test elements have been positioned in an incubator assembly 80, FIG. 3, of the automated apparatus 60, FIG. 3.

Following the preceding operation, the patient sample can be incubated and then the test element can be moved to the centrifuge 90, FIG. 3, of the apparatus 60, FIG. 3, wherein the test element 150 can be spun down in advance of a subsequent detection of an agglutination reaction, if any, between the bound matrix and the red blood cells of the sample. Exemplary operations of this type are described in commonly-assigned U.S. Pat. No. 5,911,000 to Shen, the contents of which are herein incorporated by reference in their entirety.

PARTS LIST FOR FIGS. 1-13

20 gel card
26 support member (planar substrate)
27 top side
28 bottom side
30 bead cassette
34 microtubes (test column)
37 upper portion
38 gel material
39 inwardly tapering transitional portion
41 lower portion
42 bead matrix
50 foil wrap
54 label
55 bar code
58 panel
60 automated testing apparatus
64 frame
70 sample and reagent supply
74 sample rack
76 tube hold-down assembly
77 drive means
78 reagent rack
79 bar code reader
80 incubator station
82 cassette rack
84 first section
86 second section
88 motor
90 centrifuge
94 rotor
98 motor
100 analysis station
102 holding means
104 illumination means
106 imaging subsystem
108 processing subsystem 110 transport subsystem
112 bar code reader
115 storage rack
116 waste receptacle
120 pipette assembly
122 shallow wash area
124 pipette
125 deep wash area
127 cell dilution racks
128 robot arm
130 transport assembly
134 robot arm
138 gripper
140 piercing assembly
144 support subassembly
146 piercing needles
150 test element
154 weakened or pre-stressed portions
170 punch
176 punch head
180 metering tip member
181 direction
182 cylindrical body
183 sample
184 upper tip opening
186 lower tip opening
188 interior
189 metering mechanism
190 drawer assembly
192 drawer
194 slide tray
195 motor
196 sensor bar
197 holding area
198 bar code reader It will be understood that numerous variations and modifications are possible within the ambits of the inventive concepts described herein, as provided in the following claims.

The invention claimed is:

1. An immunodiagnostic testing apparatus comprising:
a sample supply;
a metering station;
at least one test element comprising:
  a supporting member;
  at least one test column supported by the supporting member, the at least one test column containing a predetermined quantity of an inert test material and having an opening; and
  a wrap covering the opening of the at least one test chamber;
  a plurality of metering tip members;
  a mechanism configured for locally pre-stressing the wrap, such that the mechanism is configured to deform at least one portion of the wrap, such that the wrap is curved inwardly towards the contents of the at least one test column, thereby creating at least one weakened wrap portion without piercing the wrap;
and wherein the mechanism comprises a concave punch head configured to be placed in contact with the wrap portion.

2. The apparatus as recited in claim 1, wherein the opening of the test column including a peripheral edge against which the concave punch head engages to create the at least one weakened wrap portion.

3. The apparatus as recited in claim 1, wherein the metering station includes one of the plurality of metering tip members that is secured to a proboscis and in which the metering station lowers the secured metering tip member to engage and pierce the at least one weakened wrap portion of the test element.

4. The apparatus as recited in claim 3, wherein the metering tip member contains a quantity of sample for dispense into the at least one test chamber.

5. The apparatus as recited in claim 4, wherein the metering station is configured to lower the metering tip member to pierce the deformed wrap portion and to further lower the metering tip into the at least one test chamber for dispensing of the sample in a single operation.

6. The apparatus as recited in claim 1, wherein the metering tip members are disposable.

7. The apparatus as recited in claim 1, wherein the wrap is made from a foil.

8. The apparatus as recited in claim 1, wherein the at least one test element is a test card and in which the inert test material includes one of beads or a gel.

9. A test element used in an immunodiagnostic test apparatus, the test element comprising:
a planar support substrate;
a plurality of test columns supported by or integral to the support substrate, each of the test columns having an opening and containing a predetermined quantity of an inert test material within an interior of each test column; and
a wrap directly covering the opening of the test columns, the wrap including locally pre-stressed wrap portions created over each opening, each of the pre-stressed wrap portions being weakened areas that are inwardly curved towards the interior of each test column, but wherein the weakened areas are not punctured.

10. The test element as recited in claim 9, wherein the inert test material includes one of beads or a gel.

11. The test element as recited in claim 10, in which the opening of each test column is defined by a peripheral edge that serves as the outer boundary of each deformed wrap portion, which is defined by a bowl-shaped and concave configuration.

12. The test element as recited in claim 9, wherein the wrap is pierceable but in which the weakened areas permit a reduced puncture force that can be applied by a metering tip member.

13. The test element as recited in claim 12, in which the wrap is made from a foil.

* * * * *